US008500675B2

(12) United States Patent
Hamboly

(10) Patent No.: US 8,500,675 B2
(45) Date of Patent: *Aug. 6, 2013

(54) MULTILUMEN CATHETER WITH PRESSURE RESISTANT LUMEN AND METHOD

(76) Inventor: M. Samy Ahmed Hamboly, 10th of Ramadan (EG)

( * ) Notice: Subject to any disclaimer, the term of this patent is extended or adjusted under 35 U.S.C. 154(b) by 0 days.

This patent is subject to a terminal disclaimer.

(21) Appl. No.: 13/297,347

(22) Filed: Nov. 16, 2011

(65) Prior Publication Data

US 2012/0123259 A1    May 17, 2012

Related U.S. Application Data

(60) Continuation of application No. 10/905,787, filed on Jan. 20, 2005, now Pat. No. 7,740,780, and a division of application No. 12/711,015, filed on Feb. 23, 2010, now Pat. No. 8,257,298.

(51) Int. Cl.
*A61M 1/00* (2006.01)

(52) U.S. Cl.
USPC ................ 604/27; 604/43; 604/264; 604/523

(58) Field of Classification Search
USPC ........................... 604/27, 29, 43–45, 264, 523
See application file for complete search history.

(56) References Cited

U.S. PATENT DOCUMENTS

| | | | |
|---|---|---|---|
| 4,411,654 A | 10/1983 | Boarini | |
| 5,180,372 A | 1/1993 | Vegoe et al. | |
| 5,360,397 A | 11/1994 | Pinchuk | |
| 5,718,692 A | 2/1998 | Schon | |
| 5,776,111 A | 7/1998 | Tesio | |
| 5,947,953 A | 9/1999 | Ash et al. | |
| 6,001,079 A | 12/1999 | Pourchez | |
| 6,190,349 B1 | 2/2001 | Ash | |
| 6,524,302 B2 * | 2/2003 | Kelley | 604/523 |
| 6,695,832 B2 | 2/2004 | Schon | |
| 6,758,836 B2 * | 7/2004 | Zawacki | 604/284 |
| 6,849,062 B2 * | 2/2005 | Kantor | 604/103.04 |
| 6,881,211 B2 | 4/2005 | Schweikert et al. | |
| 7,018,374 B2 | 3/2006 | Schon | |
| 7,740,780 B2 | 6/2010 | Hamboly | |
| 7,981,093 B2 | 7/2011 | Schon | |
| 8,257,298 B2 * | 9/2012 | Hamboly | 604/27 |
| 2003/0153898 A1 | 8/2003 | Schon | |
| 2004/0054321 A1 | 3/2004 | Schon | |
| 2004/0059314 A1 | 3/2004 | Schon | |
| 2004/0075198 A1 | 4/2004 | Schweikert | |
| 2004/0092863 A1 | 5/2004 | Raulerson | |

* cited by examiner

*Primary Examiner* — Theodore Stigell
(74) *Attorney, Agent, or Firm* — Decker, Jones et al.; Brian K. Yost; Geoffrey A. Mantooth

(57) ABSTRACT

The assembly comprises two or more catheter tubes fused together to form a fused catheter bundle. Each tube has at least one lumen extending longitudinally through the catheter from its distal end to its proximal end and wherein at least one of said tubes comprises a pressure resistant lumen. The tubes are fused together by use of heat & pressure generated by heat shrinkable tube slides positioned over a segment of the catheter tubes while mandrels are positioned within each tube lumen. After cooling, the heat shrinkable tube may be removed and the mandrels removed such that and the fused catheter bundle is formed. One or more of the tubes may be of a different hardness, material and/or color. A distal end of the fused catheter bundle can be split free floating, stepped or tapered tipped. A non fused portion may form catheter extension legs.

3 Claims, 4 Drawing Sheets

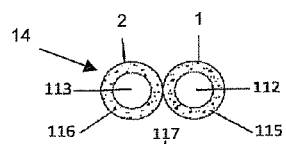
Fig. 1 A
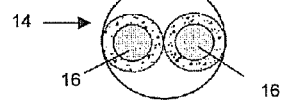
Fig. 1 B
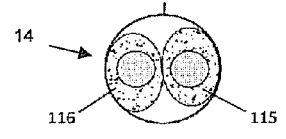
Fig. 1 C
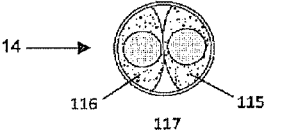
Fig. 1 D
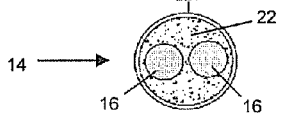
Fig. 1 E
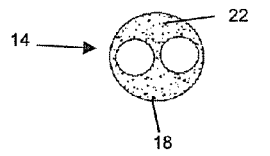
Fig. 1 F
Figures 1 A – 1 F
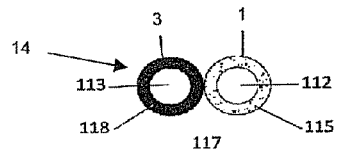
Fig. 2 A
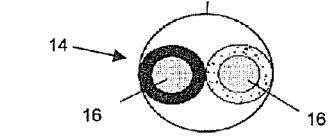
Fig. 2 B
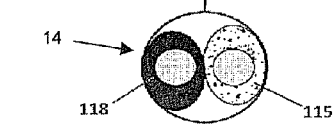
Fig. 2 C
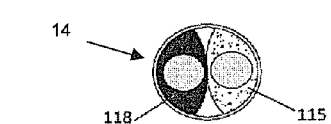
Fig. 2 D
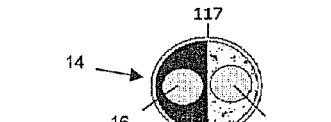
Fig. 2 E
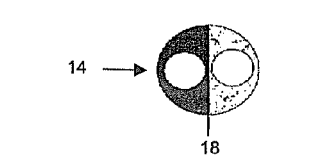
Fig. 2 F
Figures 2 A – 2 F

MULTILUMEN CATHETER WITH PRESSURE RESISTANT LUMEN AND METHOD

This application is a continuation in part patent application of application Ser. No. 10/905,787 filed Jan. 20, 2005, which was granted a patent on Jun. 22, 2010, U.S. Pat. No. 7,740,780, and divisional application Ser. No. 12/711,015 filed Feb. 23, 2010. Applicant incorporates by reference the Ser. Nos. 10/905,787 and 12/711,015 disclosures and claims the benefit of said applications.

BACKGROUND OF THE INVENTION

1. Field of the Invention

The present invention relates generally to a multitube catheter assembly, and more particularly to a multitube catheter assembly comprising one or more pressure resistant lumens.

2. Description of the Prior Art (A) Technical Background

Catheters for the introduction or removal of fluids may be located in various venous locations and cavities throughout the body for the introduction or removal of fluids. Such catheterization may be performed by using a single catheter having multiple lumens.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through a syringe needle or other introducer device, into the interior of the vessel. The introducer device is then removed leaving the guide wire within the vessel. The guide wire projects beyond the surface of the skin.

At this point, several options are available to a physician for catheter placement. The simplest is to pass a catheter into the vessel directly over the guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator are removed.

A central venous catheter ("central line") is a catheter placed within a large vein in the neck, chest, or groin. It is generally used to administer chemotherapeutic agents or other IV medications or fluids and to obtain blood tests and measurements. The overall safety and use of conventional and commercially available central venous catheters for these indications is well known. However, nearly twenty percent of central line recipients also require a CT scan. Although these patients frequently undergo IV contrast-enhanced CT as part of their clinical examination and follow-up, the feasibility and safety of using central venous catheters to administer IV contrast material using a power injector has not been well established. Because many patients requiring central venous catheters have poor peripheral IV access, it is both practical and often necessary to administer IV contrast material through the central venous catheter. Such administration is also more convenient for the patient.

The viscosities of the contrast media required in procedures such as a CT with contrast are high and an amount of up to 200 ml may be needed to be injected in a very short period of time. In general, consistent vascular enhancement and high levels of hepatic enhancement can be achieved when rapid infusion rates and appropriate delay times are used.

U.S. Pat. No. 6,524,302 issued to Kelley describes a multilumen catheter and method of manufacturing same in which the catheter comprises a plurality of individual catheter tubes. Each catheter tube has an outer surface, an inner surface and a lumen. The catheter tubes can be made of different thermoplastic materials. A mandrel is first inserted into the lumen of each catheter tube to provide support. The catheter tubes are then juxtaposed to each other in an arrangement. The outer surface of one catheter tube is in contact with the outer surface of at least one other catheter tube in the arrangement. The arrangement of catheter tubes is then held in a sleeve and is advanced through the sleeve, and through a heating cylinder to fuse the outer surfaces of the catheter tubes. A cooling means is placed in the lumen of each catheter tube to prevent the inner surface of each catheter tube from melting. Kelley teaches a catheter tube bundle formed by the fusing of the individual catheter tube material.

The Kelley bundle does not have a generally circular outside configuration. Also, the individual tubes that comprise the Kelley catheter tube bundle are fused with one another in such a manner as to result in the presence of fused material between each individual tube. However, the Kelley fused material to these spaces and does not extend to the areas, for example, where the individual catheter tubes do not meet. Therefore, Kelley provides for a fused bundle with a shape that conforms to the number of individual catheter tubes employed. For example, when three tubes are used, the fused bundle has a clover leaf shape. When two tubes are used, the fused bundle has a figure eight shape. Kelley does not teach a way to control the surface or the size of the resulting fused tube as the cross-section of the Kelley multilumen catheter has an outer periphery with at least three distinct lobes, each lobe corresponding to one of the fused tubes and not a circular outer surface configuration. Also, an additional lumen is created from the outer surfaces of the three fused catheter tubes.

(B) Manufacturing Background

U.S. Pat. Publication No. 2003/0153898 ("Schon") teaches methods for making a multilumen catheter. The methods include forming a unitary catheter tube having a proximal portion, a distal portion, and a distal end portion terminating in a distal end tip. The unitary catheter tube may be formed using any suitable heat molding process, including injection molding, expansion/compression molding, and extrusion. The unitary catheter tube is formed by extrusion through a die to form internal lumens; the lumens are substantially identical in size, configuration, and materials. The unitary catheter tube, with internal longitudinally extending lumens, may also be formed by injection molding the tube around metal rods which have the shape of the internal lumens.

However, the methods and catheters taught by Schon do not provide a fused catheter bundle with a pressure resistant lumen with circular lumens and outside configuration.

U.S. Pat. No. 6,190,349 ("Ash") teaches a multiple catheter assembly having an outer surface defining a first lumen. A second catheter has an outer surface defining a second lumen extending through the full length of their respective catheters. The lumens each have a generally semi-circular cross section. Accordingly, the first catheter has an outer surface defined by a rounded wall portion and a generally flat side surface, and the second catheter also has an outer surface defined by a rounded wall portion and a generally flat side surface, as viewed in cross section. The flat side surfaces face each other.

However, the methods and catheters taught by Ash do not provide a fused catheter bundle with a pressure resistant lumen with circular lumens and outside configuration.

There exists a need for a fused multiple catheter assembly and a method for manufacturing same, which is suitably flexible, easily inserted and which will reduce the potential risk of leakage at the site of vessel entry, but which will still maintain some of the original properties of the individual catheter tubes with respect to independent movement within a vessel, good flow properties, and pressure resistance.

Generally, the multilumen catheter design of the present invention, due to its rounded inner lumen, decreases the resistance effect to the flow of fluids, including a particularly viscid material such as contrast media. The multilumen design presented herein produces higher flow rates. Moreover, one of the fused tubes is made from a higher grade material, such as PEBA, that will resist higher internal pressure and result in a pressure resistant lumen. The higher laminar flow rate and resistance to pressure make the catheter suitable for the powerful injection of contrast media where flow may be needed at a rate of up to 10 ml/sec. A catheter constructed in accordance with the present disclosure with two tubes of different hardness levels, lowers the overall catheter rigidity than if it the catheter were totally made from the harder material which is much safer and comfortable for the patients.

SUMMARY OF THE INVENTION

A multitube catheter assembly comprising two or more catheter tubes fused together to form a fused catheter bundle comprising one or more pressure resistant lumens is provided. Each catheter tube comprises at least one lumen extending longitudinally through the catheter tube from a distal end to a proximal end. The tubes may be of the same or different materials and may have different, sizes, shapes, thicknesses, strengths, pressure resistant qualities, and other physical properties and configurations. Both tubes are preferably formed of thermoplastic elastomer materials having similar glass transition temperatures and/or melting points. The tubes may be constructed from a polyether block amide ("PEBA") material, thermoplastic polyurethane ("TPU"), or other suitable conventional and commercially available catheter material. PEBA, for example, is a high performance thermoplastic elastomer known for its flexibility and favorable mechanical properties at low and high temperatures. TPU has many useful properties, including elasticity, transparency, and resistance to oil, grease and abrasion. Fusion can occur between a PEBA and a TPU. Heating the materials above their respective glass transition temperatures or even above their respective melting points may be required depending on the similarity or dissimilarity of the materials.

The tubes are fused together by use of heat and pressure. The resulting fused catheter assembly comprises a unitary fused catheter bundle with individual lumens, one or more of which will retain the pressure resistant qualities of the original catheter tube. When heat and pressure are applied at the designated temperature and force, the molecules from each tube surface end mix. As the joint cools, the molecules return to their crystalline form, due to interdiffusion of polymer chains across the interface. The original interfaces may be removed and the two tubes will have become one continuous length. The end result is a fusion joint that is as strong as the tube itself. A wall between the two lumens results from the fusion process. This wall comprises a layer of one material irreversibly joined to a layer of the other.

The multitube catheter assembly may have distal split independent free floating ends, a stepped tip end, or tapered tip end. The lumens of the multitube catheter may be fully circular where they extend through a distal end of the fused catheter bundle, a main portion of said bundle, and the proximal end of an extension part. One or more of the lumens is surrounded by material capable of withstanding greater pressure than ordinary catheters such that the assembly may be used in procedures requiring higher pressure injections such as the infusion of contrast media. The multitube catheter assembly with pressure resistant lumen may be used in any medical field in which access to the central venous system is required such as infusion, transfusion, hemodialysis, hemofiltration, plasma exchange, chemotherapy infusion and the like.

The fused assembly results from the fusion between two or more tubes fused together. Each tube comprises at least one lumen extending longitudinally through the catheter from its distal end to its proximal end. The manner in which the fusion occurs and the degree of heat and pressure applied, allow the catheter tubes to be unreleasably joined.

In another aspect of the present invention, the catheter tube assembly, the distal end tubes, and the lumens, can also have a different shape or configuration at different points along a respective longitudinal length of each.

In another aspect of the present invention, through the use of the heat shrinkable tube, the outer wall of the fused catheter bundle, the outer wall of the distal end tubes, and the lumens, can have various shapes in cross section, such as but not limited to a circular, semi-circular, or oval shape.

The present invention also provides a method for making a multitube catheter assembly with one or more pressure resistant lumens by fusing two or more tubes together by use of a heat shrinkable tube slide positioned over and surrounding the tubes while mandrels are positioned within each lumen to protect the lumens during fusion. The heat shrinkable tube will generate pressure once heat is applied. Heating will melt/reshape the catheter tubes inside the heat shrinkable tube while the latter will not be affected due to its high melting temperature. After cooling the heat shrinkable tube is removed around the fused catheter tubes, the mandrels pulled back from the tubes, forming the fused catheter bundle. In the preferred embodiment, the mandrels are metallic. The distal end of the now fused catheter bundle may have a tapered tip resulting in a multitube tube catheter comprising a distal tapered tip end and a pressure resistant lumen.

In another aspect of the invention a method for making a multitube catheter assembly, by fusing two or more tubes together by use of an elastic tube stretched and extended over the tubes while metallic mandrels are positioned within each lumen to protect the lumens during fusion. The elastic tube will compress the catheter tubes and, upon heating, will melt/reshape the catheter tubes inside the elastic tube while the latter will not be affected due to its high temperature resistance. After cooling the elastic tube is removed from the fused catheter tubes and the metallic mandrels pulled back from the tubes to reveal a newly, formed fused catheter bundle. The elastic tube can be formed from silicon, rubber or other materials equivalent thereto.

In another aspect of the invention, the absence of a connector or a hub between catheter shaft and extension line allows the catheter to be advanced and positioned to any desirable length then fixed with any fixation devices.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention in the drawings:

FIG. 1A is a cross sectional view of a multitube catheter assembly before the shrinkable tube is positioned and before fusion begins in accordance with a prior embodiment.

FIG. 1B is a cross sectional view of a multitube catheter assembly after the shrinkable tube has been positioned and before fusion begins in accordance with a prior embodiment.

FIG. 1C is a cross sectional view of a multitube catheter assembly after the shrinkable tube has been positioned and during the fusion process in accordance with a prior embodiment.

FIG. 1D is a cross sectional view of a multitube catheter assembly after the shrinkable tube has been positioned and during the fusion process, in accordance with a prior embodiment.

FIG. 1E is a cross sectional view of a multitube catheter assembly after the fusion process has completed with the shrinkable tube still positioned, in accordance with a prior embodiment.

FIG. 1F is a cross sectional view of a multitube catheter assembly after the fusion process has completed with the shrinkable tube removed, in accordance with a prior embodiment.

FIG. 2A is a cross sectional view of a multitube catheter assembly with a pressure resistant lumen before the shrinkable tube is positioned and before fusion begins, in accordance with a preferred embodiment.

FIG. 2B is a cross sectional view of a multitube catheter assembly with a pressure resistant lumen after the shrinkable tube has been positioned and before fusion begins, in accordance with a preferred embodiment.

FIG. 2C is a cross sectional view of a multitube catheter assembly with a pressure resistant lumen after the shrinkable tube has been positioned and during the fusion process, in accordance with a preferred embodiment.

FIG. 2D is a cross sectional view of a multitube catheter assembly with a pressure resistant lumen after the shrinkable tube has been positioned and during the fusion process, in accordance with a preferred embodiment.

FIG. 2E is a cross sectional view of a multitube catheter assembly with a pressure resistant lumen after the fusion process has completed with the shrinkable tube still positioned, in accordance with a preferred embodiment.

FIG. 2F is a cross sectional view of a multitube catheter assembly with a pressure resistant lumen after the fusion process has completed with the shrinkable tube removed, in accordance with a preferred embodiment.

FIG. 6 is a cross section of FIG. 3 at the lines VI-VI.
FIG. 7 is a cross section of FIG. 3 at the lines VII-VII.
FIG. 8 is a cross section of FIG. 3 at the lines VIII-VIII.
FIG. 9 is a cross section of FIG. 4 at the lines IX-IX.
FIG. 10 is a cross section of FIG. 4 at the lines X-X.
FIG. 11 is a cross section of FIG. 4 at the lines XI-XI.
FIG. 12 is a cross section of FIG. 5 at the lines XII-XII.
FIG. 13 is a cross section of FIG. 5 at the lines XIII-XIII.
FIG. 14 is a cross section of FIG. 5 at the lines XIV-XIV

DESCRIPTION OF THE PREFERRED EMBODIMENT

Figure 3:
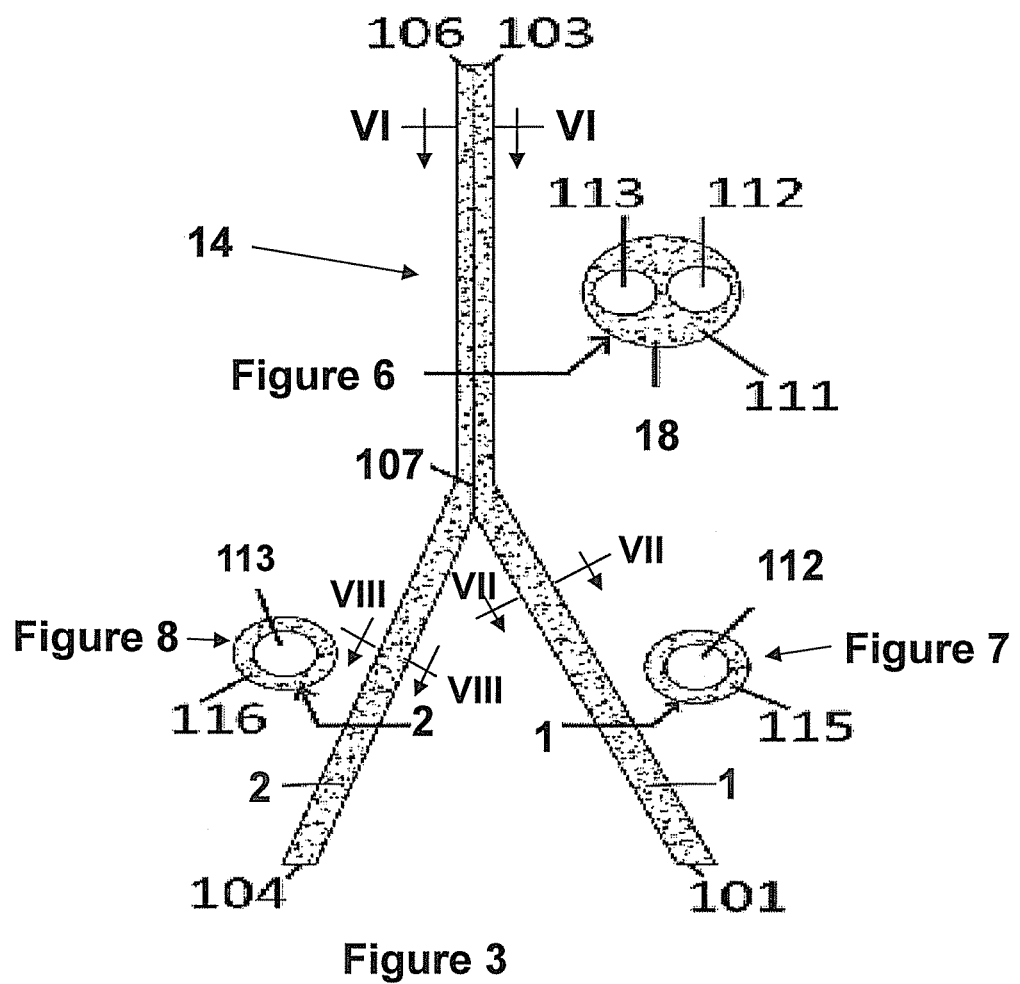
FIG. 3 is a top plan view of the catheter assembly formed as result of fusion between proximal parts of two tubes, in accordance with a prior embodiment.

In describing the embodiments of the invention illustrated in the drawings, specific terminology will be used for the sake of clarity. However, the invention is not intended to be limited to the specific terms so selected, it being understood that each specific term includes all technical equivalents operating in similar manner to accomplish similar purpose. It is understood that the drawings are not drawn exactly to scale. In the drawings, similar reference numbers are used for designating similar elements throughout the several drawings.

The following describes particular embodiments of the invention. However, it should be understood, based on this disclosure, that the invention is not limited to the embodiments detailed herein. Generally, the following disclosure refers to dual or multiple lumen catheter assemblies, although catheter assemblies having more lumens and/or distal end tubes are within the scope of the invention. Further, the methods described below for making the catheter assemblies of the present invention are also applicable to making catheter assemblies having more than two lumens and/or distal end tubes. It is only for reasons of convenience that the following description refers to two or three lumen embodiments of the present invention.

The multitube catheter assemblies of the present invention may be inserted into an area of a body of a patient to be catheterized for removing and introducing fluids to the body. The catheter assemblies of the present invention may be secured to a fixed location in or on the patient body, such as a subcutaneous area, before the catheter assembly is properly inserted and positioned in the area to be catheterized. This method is particularly preferred for long term catheterization. Alternatively, in short term catheterization, the catheter assemblies of the present invention may be secured to an external surface of the body before or after the catheter assembly is properly inserted and positioned in the area to be catheterized.

The multitube catheter assemblies of the present invention can be adapted for use in various applications in which bodily fluids, medicines, medicaments, or other solutions are introduced into and removed from the body, such as infusion, transfusion, plasmapheresis, hemodialysis, chemotherapy, and the like. The area to be catheterized is preferably a blood vessel, such as an internal jugular vein, but may be any suitable area within the body. Other areas in which the catheter assemblies may be used include other blood vessels, including the femoral and subclavian veins, any cavity, and other areas of the body including intra-abdominal, sub-diaphragmatic and sub hepatic areas. It is understood that the above-referenced areas are exemplary, and that the catheter assemblies of the present invention may be used to remove or introduce fluids to various areas to be catheterized.

The preferred embodiments of the present invention shown in the drawings are particularly useful for infusion and transfusion of fluid into a blood vessel, such as the internal jugular vein and powerful injection of a viscid fluid such as contrast media.

The embodiments of the present invention shown in the drawings are also useful for intake, or removal, of blood to be purified from a blood vessel, such as the internal jugular vein, and introduction of purified blood into the same vessel. The blood can be purified by any suitable hemodialysis apparatus attached in communication with lumens of the disclosed catheter assemblies.

For purposes of describing the embodiments of the present invention shown in the drawings, the catheter assemblies will be described with respect to an application of channeling to the venous system. However, it is understood that the catheter assemblies of the present invention can be configured and adapted, by increasing or decreasing a size (diameter or length) and/or number of distal end tubes and/or lumens in the respective catheter assembly, so that the catheter assembly can be beneficially used for other medical applications in which fluids are introduced into and/or removed from the body.

Referring to the Figures, FIGS. 1A-1F, there is illustrated a prior embodiment of the catheter assembly depicting the catheter tube 1, 2 cross sectional changes that occur during the fusion process. Referring to FIG. 1A, the first tube 1 and the second tube 2 which are of the same material and color and which have generally round outer surface configurations, circular lumens 112, 113, and walls 115, 116. FIG. 1B illustrates the presence of the heat shrinkable tube slide 117 positioned over the first and second tube 1, 2. Round mandrels 16, 16 positioned within each lumen 112, 113 protect the lumens 112, 113 during the fusion process. When heat is applied, the heat shrinkable tube 117 contracts and generates pressure over catheter tubes 1, 2. Continued heating melts/reshapes the catheter tubes 1, 2 within the heat shrinkable tube 117 while the latter 117 is not affected due to its relative high melting temperature. Referring to FIGS. 1C and 1D, continued heating melts the walls 115, 116 of the first and second tubes 1, 2. Referring to FIG. 1E, the walls 115, 116 fuse together forming one wall 22 defining the catheter tube 118 around the catheter lumens 112, 113. After cooling, the heat shrinkable tube 117 may be removed from the newly formed fused catheter bundle 18 and the mandrels 16, 16 may be withdrawn from the catheter lumens 112, 113. Referring to FIG. 1F, the fused catheter bundle 18 is formed with the wall 22 surrounding the fused material that forms catheter lumens 112, 113.

In accordance with a preferred embodiment, FIGS. 2A-2F illustrate the multitube catheter assembly with pressure resistant lumen assembly's 14 tubes' 1, 3 cross sectional changes that occur during the fusion process. Referring to FIG. 2A, the first tube 1 and the second tube 3 which are of different material hardness or color have generally round outer surface configurations and circular lumens 112, 113 and walls 115, 118. Both tubes 1, 3 are preferably formed of thermoplastic elastomer materials having similar glass transition temperatures and/or melting points. The tubes 1, 3 may be constructed from a polyether block amide ("PEBA") material, thermoplastic polyurethane ("TPU"), or other suitable conventional and commercially available catheter material. PEBA, for example, is a high performance thermoplastic elastomer known for its flexibility and favorable mechanical properties at low and high temperatures. TPU has many useful properties, including elasticity, transparency, and resistance to oil, grease and abrasion. Fusion can occur between a PEBA and a TPU. Heating the materials 1, 3 above their respective glass transition temperatures or even above their melting points may be required depending on the similarity or dissimilarity of the materials 1, 3. In the preferred embodiment, tube 3 is a catheter tube 3 comprising a pressure resistant lumen 113 and is preferably formed from PEBA material. FIG. 2B illustrates the presence of the heat shrinkable tube 117 positioned over the first and second tubes 1, 3. Round mandrels 16, 16 positioned within each lumen 112, 113 protect the lumens 112, 113 during the fusion process. When heat is applied, the heat shrinkable tube 117 contracts and generates pressure over catheter tubes 1, 2. Continued heating melts/reshapes the catheter tubes 1, 2 within the heat shrinkable tube 117 while the latter 117 is not affected due to its relative high melting temperature. Referring to FIGS. 2C and 2D, continued heating melts the walls 115, 116 of the first and second tubes 1, 2. Referring to FIG. 2E, the walls 115, 116 fuse together forming one wall 22 defining the fused catheter bundle 14 and which surrounds the material that forms the catheter lumens 112, 113. After cooling, the heat shrinkable tube 117 may be removed from the newly formed fused catheter bundle 20 and the mandrels 16, 16 may be withdrawn from the catheter lumens 112, 113. Referring to FIG. 2F, the fused catheter bundle 20 is formed with the wall 22 surrounding material that forms catheter lumens 112, 113.

FIG. 3 illustrates a prior embodiment of the catheter assembly 14 shown in FIG. 1F and comprises at least two lumens 112, 113. The illustration of two lumens 112, 113 is exemplary, and the scope of the invention encompasses catheter assemblies 14 comprising more than two lumens 112, 113.

Figure 4:
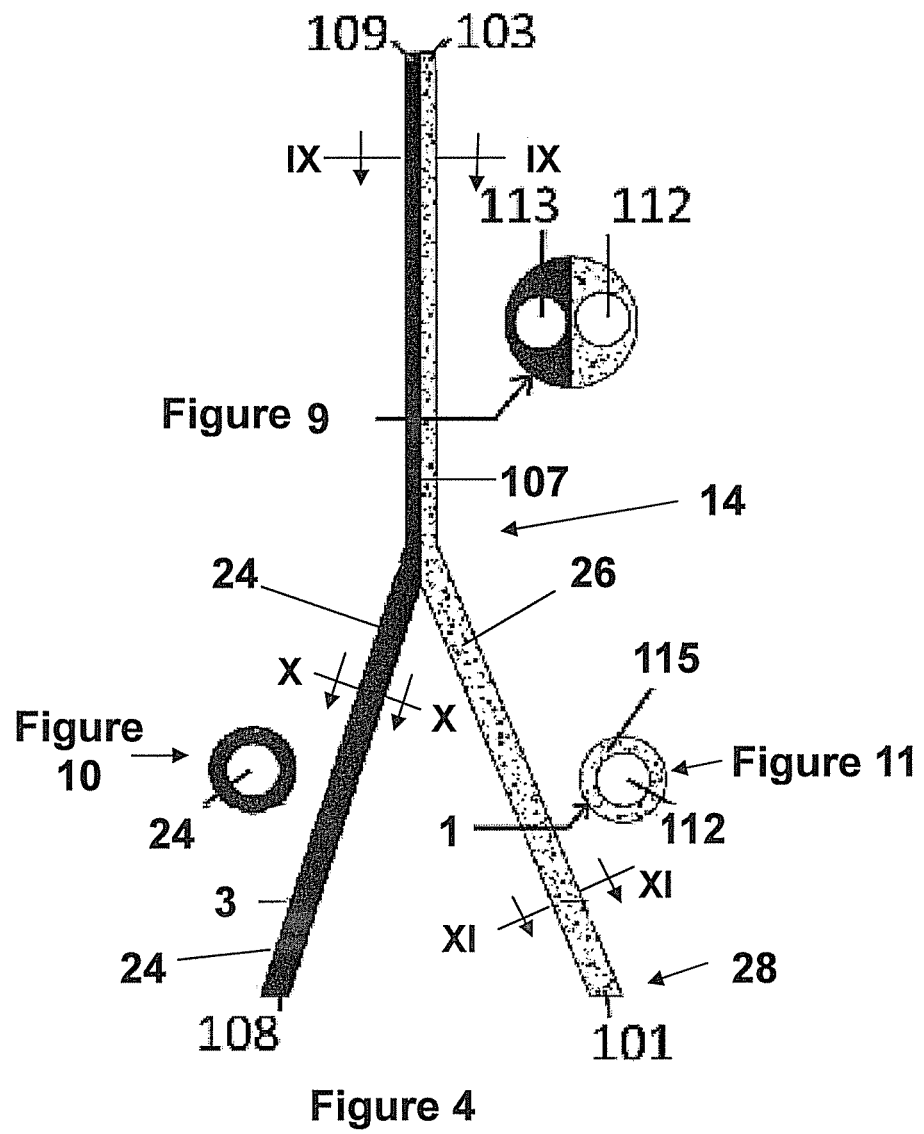
FIG. 4 is a top plan view of the catheter assembly with a pressure resistant lumen formed as result of fusion between proximal parts of two tubes, in accordance with a preferred embodiment.

FIG. 4 illustrates a catheter assembly with pressure resistant lumen 14 in accordance with a preferred embodiment and which comprises at least two lumens 112, 113. The illustration of two lumens 112, 113 is exemplary, and the scope of the invention encompasses catheter assemblies 14 comprising more than two lumens 112, 113.

The catheter assembly 14 shown in FIG. 4 comprises first tube 1 which has a distal end 101 and a proximal end 103. The catheter assembly 14 comprises a second tube 3 which is of different material, hardness or color and has a proximal end 108 and a distal end 109. FIGS. 5A and 5B illustrate cross sections of tubes 1 and 3. Tube 1 comprises lumen 112 and wall 115. Tube 3 comprises lumen 113 and wall 118.

The first and second tubes 1, 3 are united or fused at point 107 forming fused catheter bundle 20 as a result of fusion of a portion of walls 112 and 118.

The multi-lumen catheter assembly with pressure resistant lumen 14 comprises a first lumen 112 and a second lumen 113 extending longitudinally therethrough as illustrated in FIG. 2. The first and second lumens 112, 113 are continuous with and through the first and second tubes 1, 3 from the proximal end 30, the fused catheter bundle 20 and extension tubes 24 and 26. The first and the second extension tubes 24 and 26 lead to a distal end 28 of the catheter assembly 14, through which the materials entering and/or exiting the patient enter and/or exit the catheter assembly 14. The words "proximal" and "distal" refer to directions away from and closer to, respectively, the inserted end of the catheter assembly 14.

The exterior of the fused catheter bundle 20 of the present embodiment comprises a smooth, rounded configuration without ridges or grooves.

As shown in FIG. 2F, the outer surface or outside configuration of the fused catheter bundle 20 is generally rounded in shape. FIG. 2F illustrates in cross-section a generally round shaped outer wall, with the first and the second lumens 112, 113 comprising a circular cross-section. However, the fused catheter bundle 20 can have various shapes, such as but not limited to circular, semi-circular or oval. Also, lumens 112, 113 can have various cross section shapes, such as, but not limited to, circular, semi-circular or oval shapes.

In the above mentioned embodiments, it is noted that the distal ends 101, 108 may occur at different locations in various catheters assemblies 14. It is within the scope of the present invention to incorporate, in the dimensional aspects of length disclosed above, all locations where the distal ends 101, 108 could be said to occur in catheters 14 known in the art, disclosed herein, or to be developed. The assembly 14 according to the preferred embodiment comprises incorporating different connectors to the distal ends 101, 108 to form distal catheter hubs.

The smooth generally rounded exterior surface of fused catheter bundle 20 passes through and remains positioned at a vessel wall insertion site during insertion of the catheter assembly into a patient. A vessel wall seals quite well around the smooth, round exterior surface of fused catheter bundle 20 as shown in cross-section FIG. 2F. Since the exterior of fused catheter bundle 20 provides a good seal at the insertion site, the risk of blood loss around the catheter assembly 14 at the insertion site is minimized.

The first and the second lumens 112, 113 are generally circular since circular cross sections are most conducive to fluid flow properties. However, other shapes such as D-shaped passageways and/or lumens 112, 113, oval, triangular, square, elliptical, kidney-bean shaped passageways and/or lumens 112, 113, or other configurations are also within the scope of the invention. Further, while the catheter tubes 1, 3, the lumens 112, 113 and the proximal end 28 tubes 1, 3 are preferably identical in cross section, it is within the scope of the invention to vary the size, shape and/or configuration such that smaller distal end 28 tubes 1, 3 and/or lumens 112, 113, or varying types of lumens 112, 113 and distal end 28 tubes 1, 3 may be used for other applications, such as an addition of a third, smaller lumen 112, 113 and corresponding distal end 28 tubes 1, 3 for introduction of medication.

The catheter assembly 14 according to the various embodiments may incorporate a suture wing secured or over molded over point 107.

The present invention further includes methods for making the multi-lumen catheter assemblies described above.

The fusion parameter settings allow the catheter tube to be non-releasably joined by fusing two or more tubes of different materials 1, 2, 3, hardness or color together by use of a heat shrinkable tube slide 117 over the tubes 1,2,3, while mandrels 16, 16 are passed through each tube lumen 112, 113 to protect the lumens 112, 113 during fusion. The heat shrinkable tube 117 will generate pressure once heat is applied. Continued heating will melt/re-shape the catheter tubes 1, 2, 3 inside the heat shrinkable tube 117 while the latter 117 will not be affected due to its relatively high melting temperature. After cooling, the heat shrink tube 117 is removed around the fused catheter tubes 1, 2, 3, and the mandrels 16, 16 pulled back and the tubes 1, 2, 3 forming the fused catheter bundle 20.

Figure 5:
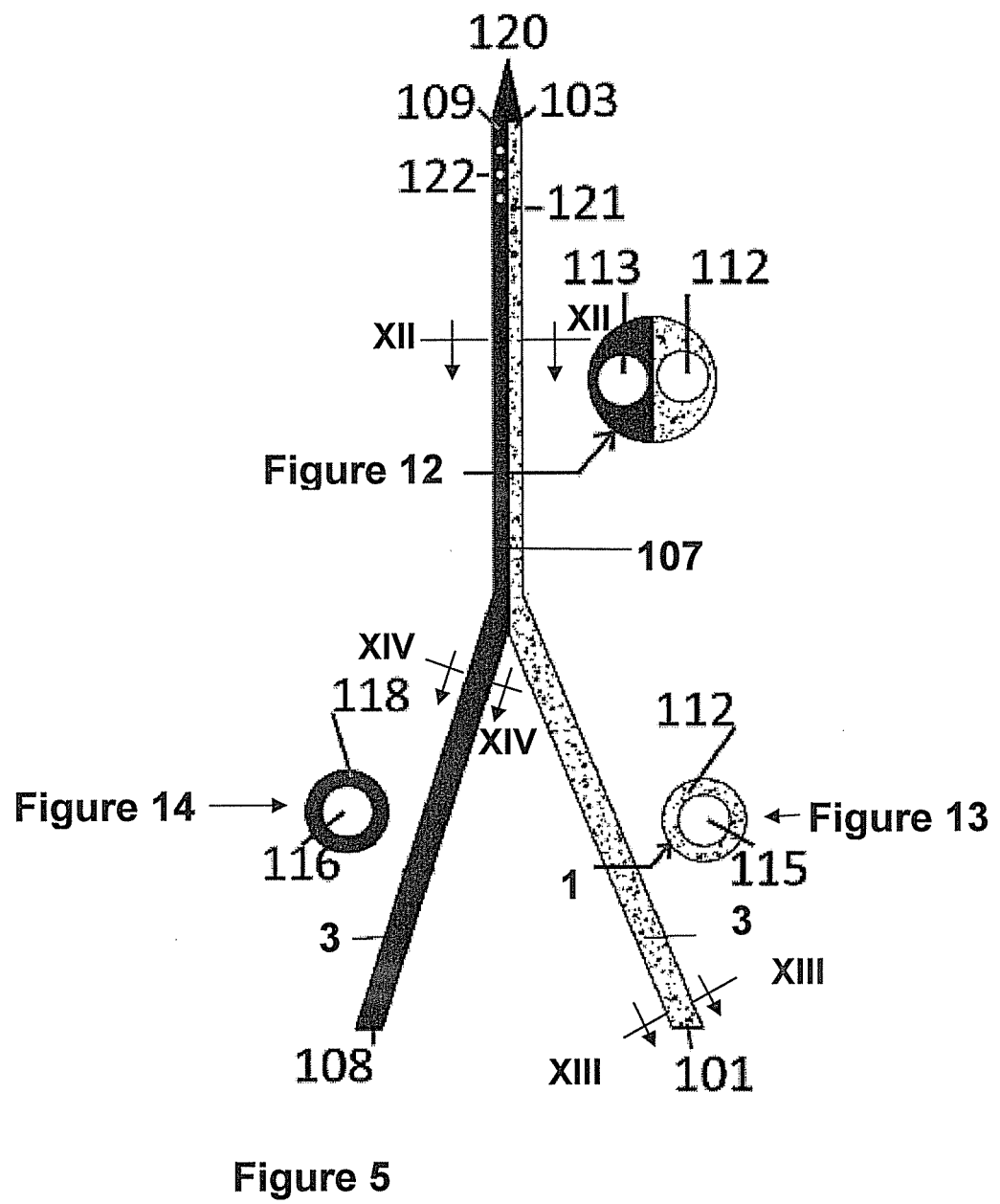
FIG. 5 is a top plan view of the catheter assembly with a pressure resistant lumen formed as result of fusion between proximal parts of two tubes, in accordance with another embodiment.

Referring to FIG. 5, there is shown an alternative embodiment of the catheter assembly 14 of FIG. 4. The assembly 14 according to this embodiment comprises tipping of the proximal end 30 of the catheter assembly 14 to form a proximal catheter tip 120.

I claim:

1. A multitube catheter assembly comprising: a plurality of tube catheters, each having a proximal opening, a distal opening and outer surface defining a lumen extending longitudinally therethrough between the respective distal and proximal openings, said lumens each having a length, the tube catheters being non-concentric with at least one of said lumens being circular throughout the length between said respective distal and proximal openings; each lumen being independent from each other; wherein a portion of the outer surface of one tube catheter is fused to at least a portion of the outer surface of at least one other tube catheter to form a fused bundle comprising a generally circular outer wall comprising fused material, such that when viewed in transverse cross section, the fused bundle comprises a generally circular outside configuration defined by said wall; wherein the lumens each have a diameter when viewed in transverse cross section; an outer boundary of said lumens being formed from fused material, said fused material being generally radially, and circumferentially distributed within a region corresponding to the outer wall and a region outside the lumen diameter, such that each lumen is substantially surrounded by fused material; said tube catheters comprising a higher pressure catheter and a lower pressure catheter, said higher pressure catheter being adapted to resist a greater tube catheter internal pressure than said lower pressure catheter.

2. The multitube catheter assembly of claim 1 wherein said higher pressure catheter is of a different color than said lower pressure catheter.

3. The multitube catheter assembly of claim 1, the catheter tubes further comprising an extension portion, said extension portion comprising catheter tubes extending from said bundle, each of said extension portion catheter tubes comprising ends, at least one of said extension portion catheter tube's end being separated from at least one other extension portion catheter tube's end.

* * * * *